(12) United States Patent
Tuval et al.

(10) Patent No.: US 9,060,855 B2
(45) Date of Patent: Jun. 23, 2015

(54) PROSTHETIC VALVE

(75) Inventors: Yosi Tuval, Netanya (IL); Igor Kovalsky, Givataim (IL)

(73) Assignee: Ventor Technologies Ltd., Netanya, IL (US)

(*) Notice: Subject to any disclaimer, the term of this patent is extended or adjusted under 35 U.S.C. 154(b) by 305 days.

(21) Appl. No.: 13/422,716

(22) Filed: Mar. 16, 2012

(65) Prior Publication Data

US 2013/0073030 A1 Mar. 21, 2013

Related U.S. Application Data

(62) Division of application No. 12/250,163, filed on Oct. 13, 2008, now Pat. No. 8,137,398.

(51) Int. Cl.
*A61F 2/24* (2006.01)

(52) U.S. Cl.
CPC ............ *A61F 2/2403* (2013.01); *A61F 2/2418* (2013.01); *A61F 2/2436* (2013.01); *A61F 2/2427* (2013.01); *A61F 2230/0013* (2013.01); *A61F 2230/005* (2013.01); *A61F 2230/0078* (2013.01); *A61F 2230/008* (2013.01)

(58) Field of Classification Search
CPC ............... A61F 2/2433; A61F 2/2442; A61F 2002/249; A61F 2/243
USPC .............. 623/1.24, 1.31–1.32, 1.36, 2.1, 2.17
See application file for complete search history.

(56) References Cited

U.S. PATENT DOCUMENTS

| 5,507,771 | A | * | 4/1996 | Gianturco | 606/198 |
|---|---|---|---|---|---|
| 5,779,732 | A | * | 7/1998 | Amundson | 623/1.15 |
| 7,823,267 | B2 | * | 11/2010 | Bolduc | 29/525.01 |
| 8,308,798 | B2 | * | 11/2012 | Pintor et al. | 623/2.18 |
| 8,926,686 | B2 | * | 1/2015 | King | 623/1.13 |
| 2001/0037142 | A1 | * | 11/2001 | Stelter et al. | 623/1.13 |
| 2005/0137689 | A1 | * | 6/2005 | Salahieh et al. | 623/2.11 |
| 2005/0182476 | A1 | * | 8/2005 | Hartley et al. | 623/1.11 |
| 2006/0142836 | A1 | * | 6/2006 | Hartley et al. | 623/1.11 |
| 2006/0149360 | A1 | * | 7/2006 | Schwammenthal et al. | 623/1.24 |
| 2006/0173475 | A1 | * | 8/2006 | Lafontaine et al. | 606/159 |
| 2006/0265056 | A1 | * | 11/2006 | Nguyen et al. | 623/2.18 |
| 2007/0032862 | A1 | * | 2/2007 | Weber et al. | 623/1.34 |
| 2007/0043425 | A1 | * | 2/2007 | Hartley et al. | 623/1.12 |
| 2007/0225797 | A1 | * | 9/2007 | Krivoruhko | 623/1.35 |
| 2008/0082165 | A1 | * | 4/2008 | Wilson et al. | 623/2.11 |
| 2008/0208332 | A1 | * | 8/2008 | Lamphere et al. | 623/2.38 |
| 2008/0269877 | A1 | * | 10/2008 | Jenson et al. | 623/2.11 |
| 2008/0294234 | A1 | * | 11/2008 | Hartley et al. | 623/1.12 |
| 2009/0216308 | A1 | * | 8/2009 | Hartley | 623/1.11 |
| 2010/0049313 | A1 | * | 2/2010 | Alon et al. | 623/2.11 |
| 2010/0168836 | A1 | * | 7/2010 | Kassab | 623/1.11 |
| 2010/0286757 | A1 | * | 11/2010 | Petersen et al. | 623/1.13 |
| 2011/0087320 | A1 | * | 4/2011 | Bolduc et al. | 623/1.35 |
| 2011/0125244 | A1 | * | 5/2011 | Roeder et al. | 623/1.11 |

(Continued)

*Primary Examiner* — Thomas J Sweet
*Assistant Examiner* — Seema Mathew (57) ABSTRACT

In some embodiments, an apparatus includes a valve prosthesis for attachment to a native valve complex of a subject. The prosthesis is configured to assume a compressed delivery state and an uncompressed implantation state. The prosthesis includes a support frame, which is shaped so as to define an upstream inlet having upstream-most portions that are tapered in an upstream direction toward a central longitudinal axis of the prosthesis when the prosthesis assumes the compressed delivery state, and a flexible prosthetic heart valve component, coupled to the support frame. Other embodiments are also described.

18 Claims, 7 Drawing Sheets

(56) References Cited

U.S. PATENT DOCUMENTS

| | | | |
|---|---|---|---|
| 2011/0264192 A1* | 10/2011 | Hartley et al. | 623/1.13 |
| 2012/0046728 A1* | 2/2012 | Huser et al. | 623/1.13 |
| 2012/0172965 A1* | 7/2012 | Kratzberg et al. | 623/1.12 |
| 2012/0239141 A1* | 9/2012 | Palmaz | 623/2.2 |
| 2012/0259406 A1* | 10/2012 | Schreck et al. | 623/1.27 |
| 2012/0277848 A1* | 11/2012 | Roeder et al. | 623/1.13 |
| 2013/0046371 A1* | 2/2013 | Greenberg et al. | 623/1.11 |
| 2013/0073032 A1* | 3/2013 | Wang | 623/2.11 |
| 2013/0109960 A1* | 5/2013 | Stinis | 600/424 |
| 2013/0116773 A1* | 5/2013 | Roeder et al. | 623/1.15 |
| 2013/0152659 A1* | 6/2013 | Maimon et al. | 72/370.25 |
| 2013/0166015 A1* | 6/2013 | Roeder | 623/1.13 |
| 2014/0005767 A1* | 1/2014 | Glazier et al. | 623/2.11 |
| 2014/0088692 A1* | 3/2014 | Wright | 623/2.11 |
| 2014/0148888 A1* | 5/2014 | Barrand | 623/1.2 |
| 2014/0148895 A1* | 5/2014 | King | 623/1.13 |
| 2014/0180378 A1* | 6/2014 | Roeder | 623/1.11 |
| 2014/0277338 A1* | 9/2014 | Kolbel et al. | 623/1.11 |
| 2015/0012080 A1* | 1/2015 | Barrand | 623/1.13 |

* cited by examiner

PROSTHETIC VALVE

CROSS-REFERENCE TO RELATED APPLICATIONS

This patent application is a divisional of U.S. patent application Ser. No. 12/250,163, filed Oct. 13, 2008, now pending, which is incorporated herein by reference in its entirety.

BACKGROUND OF THE INVENTION

1. Field of the Invention

The present invention relates generally to prosthetic heart valves, and specifically to prosthetic heart values configured for delivery using a catheter.

2. Background Art

Aortic valve replacement in patients with severe valve disease is a common surgical procedure. The replacement is conventionally performed by open heart surgery, in which the heart is usually arrested and the patient is placed on a heart bypass machine. In recent years, prosthetic heart valves have been developed which are implanted using minimally invasive procedures such as transapical or percutaneous approaches. These methods involve compressing the prosthesis radially to reduce its diameter, inserting the prosthesis into a delivery tool, such as a catheter, and advancing the delivery tool to the correct anatomical position in the heart. Once properly positioned, the prosthesis is deployed by radial expansion within the native valve annulus.

PCT Publication WO 05/002466 to Schwammenthal et al., relevant portions of which are incorporated herein by reference, describes prosthetic devices for treating aortic stenosis.

PCT Publication WO 06/070372 to Schwammenthal et al., relevant portions of which are incorporated herein by reference, describes a prosthetic device having a single flow field therethrough, adapted for implantation in a subject, and shaped so as to define a fluid inlet and a diverging section, distal to the fluid inlet.

US Patent Application Publication 2006/0149360 to Schwammenthal et al., relevant portions of which are incorporated herein by reference, describes a prosthetic device including a valve-orifice attachment member attachable to a valve in a blood vessel and including a fluid inlet, and a diverging member that extends from the fluid inlet, the diverging member including a proximal end near the fluid inlet and a distal end distanced from the proximal end. A distal portion of the diverging member has a larger cross-sectional area for fluid flow therethrough than a proximal portion thereof US Patent Application Publication 2004/0186563 to Lobbi, relevant portions of which are incorporated herein by reference, describes a prosthetic heart valve having an internal support frame with a continuous, undulating leaflet frame defined therein. The leaflet frame has three cusp regions positioned at an inflow end intermediate three commissure regions positioned at an outflow end thereof. The leaflet frame may be cloth covered and flexible leaflets attached thereto form occluding surfaces of the valve. The support frame further includes three cusp positioners rigidly fixed with respect to the leaflet frame and located at the outflow end of the support frame intermediate each pair of adjacent commissure regions. The valve is desirably compressible so as to be delivered in a minimally invasive manner through a catheter to the site of implantation. Upon expulsion from catheter, the valve expands into contact with the surrounding native valve annulus and is anchored in place without the use of sutures. In the aortic valve position, the cusp positioners angle outward into contact with the sinus cavities, and compress the native leaflets if they are not excised, or the aortic wall if they are. The support frame may be formed from a flat sheet of Nitinol that is bent into a three-dimensional configuration and heat set. A holder having spring-like arms connected to inflow projections of the valve may be used to deliver, reposition and re-collapse the valve, if necessary.

U.S. Pat. No. 7,018,408 to Bailey et al., relevant portions of which are incorporated herein by reference, describes prosthetic cardiac and venous valves and a single catheter device, and minimally invasive techniques for percutaneous and transluminal valvuloplasty and prosthetic valve implantation.

U.S. Pat. No. 6,730,118 to Spenser et al., relevant portions of which are incorporated herein by reference, describes a valve prosthesis device suitable for implantation in body ducts. The device comprises a support stent, comprised of a deployable construction adapted to be initially crimped in a narrow configuration suitable for catheterization through the body duct to a target location and adapted to be deployed by exerting substantially radial forces from within by means of a deployment device to a deployed state in the target location, and a valve assembly comprising a flexible conduit having an inlet end and an outlet, made of pliant material attached to the support beams providing collapsible slack portions of the conduit at the outlet. The support stent is provided with a plurality of longitudinally rigid support beams of fixed length. When flow is allowed to pass through the valve prosthesis device from the inlet to the outlet, the valve assembly is kept in an open position, whereas a reverse flow is prevented as the collapsible slack portions of the valve assembly collapse inwardly providing blockage to the reverse flow.

US Patent Application Publication 2006/0074485 to Realyvasquez, relevant portions of which are incorporated herein by reference, describes methods and apparatus for valve repair or replacement. In one embodiment, the apparatus is a valve delivery device comprising a first apparatus and a second apparatus. The first apparatus includes a heart valve support having a proximal portion and a distal portion and a heart valve excisor slidably mounted on said first apparatus. The second apparatus includes a fastener assembly having a plurality of penetrating members mounted to extend outward when the assembly assumes an expanded configuration; and a heart valve prosthesis being releasably coupled to said second apparatus. The first apparatus and second apparatus are sized and configured for delivery to the heart through an opening formed in a femoral blood vessel. The heart valve prosthesis support is movable along a longitudinal axis of the device to engage tissue disposed between the anvil and the valve prosthesis. The system may include a tent and/or an embolic screen to capture debris from valve removal.

U.S. Pat. No. 7,018,408 to Bailey et al., relevant portions of which are incorporated herein by reference, describes prosthetic cardiac and venous valves and a single catheter device and minimally invasive techniques for percutaneous and transluminal valvuloplasty and prosthetic valve implantation.

The following patents and patent application publications, relevant portions of which are incorporated herein by reference, may be of interest:

US Patent Application Publication 2004/0039436 to Spenser et al.

US Patent Application Publication 2005/0197695 to Stacchino et al.

U.S. Pat. No. 6,312,465 to Griffin et al.

U.S. Pat. No. 5,908,451 to Yeo

U.S. Pat. No. 5,344,442 to Deac

U.S. Pat. No. 5,354,330 to Hanson

US Patent Application Publication 2004/0260389 to Case et al.
U.S. Pat. No. 6,730,118 to Spencer et al.
U.S. Pat. No. 7,018,406 to Seguin et al.
U.S. Pat. No. 6,458,153 and US Patent Application Publication 2003/0023300 to Bailey et al.
US Patent Application Publication 2004/0186563 to Lobbi
US Patent Application Publication 2003/0130729 to Paniagua et al.
US Patent Application Publication 2004/0236411 to Sarac et al.
US Patent Application Publication 2005/0075720 to Nguyen et al.
US Patent Application Publication 2006/0058872 to Salahieh et al.
US Patent Application Publication 2005/0137688 to Salahieh et al.
US Patent Application Publication 2005/0137690 to Salahieh et al.
US Patent Application Publication 2005/0137691 to Salahieh et al.
US Patent Application Publication 2005/0143809 to Salahieh et al.
US Patent Application Publication 2005/0182483 to Osborne et al.
US Patent Application Publication 2005/0137695 to Salahieh et al.
US Patent Application Publication 2005/0240200 to Bergheim
US Patent Application Publication 2006/0025857 to Bergheim et al.
US Patent Application Publication 2006/0025855 to Lashinski et al.
US Patent Application Publication 2006/0047338 to Jenson et al.
US Patent Application Publication 2006/0052867 to Revuelta et al.
US Patent Application Publication 2006/0074485 to Realyvasquez
US Patent Application Publication 2003/0149478 to Figulla et al.
U.S. Pat. No. 7,137,184 to Schreck
U.S. Pat. No. 6,296,662 to Caffey
U.S. Pat. No. 6,558,418 to Carpentier et al.
U.S. Pat. No. 7,267,686 to DiMatteo et al.

SUMMARY

In some embodiments, an apparatus includes a valve prosthesis for attachment to a native valve complex of a subject. The prosthesis is configured to assume a compressed delivery state and an uncompressed implantation state. The prosthesis includes a support frame, which is shaped so as to define an upstream inlet having upstream-most portions that are tapered in an upstream direction toward a central longitudinal axis of the prosthesis when the prosthesis assumes the compressed delivery state, and a flexible prosthetic heart valve component, coupled to the support frame. Other embodiments are also described.

The present invention will be better understood by reference to the following detailed discussion of specific embodiments and the attached figures, which illustrate and exemplify such embodiments.

DETAILED DESCRIPTION OF THE PREFERRED EMBODIMENT

Figures 1A, 1B, 1C:
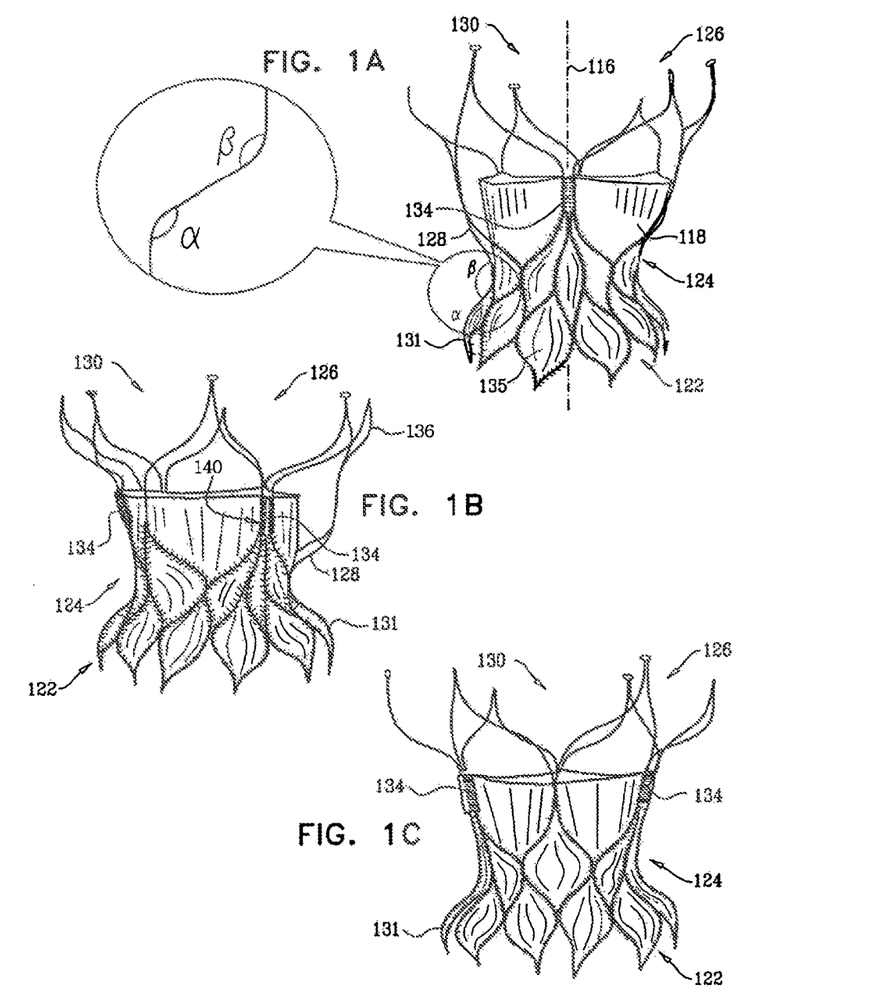
FIGS. 1A-C are schematic illustrations of a valve prosthesis, in accordance with an embodiment of the present invention.

FIGS. 1A and 1B are schematic illustrations of a valve prosthesis 130, in accordance with an embodiment of the present invention. FIG. 1A shows the prosthesis including a flexible prosthetic downstream valve component 118 and a inlet covering 135 that covers an upstream inlet 131, while FIGS. 1B and 1C, for clarity of illustration, show only a support frame 140 of the valve prosthesis, without flexible prosthetic downstream valve component 118 or inlet covering 135. Valve prosthesis 130 comprises a collapsible support frame 140, which typically comprises exactly three commissural posts 134, arranged circumferentially around a central longitudinal axis 116 of the valve prosthesis. Valve prosthesis 130 further comprises flexible prosthetic downstream valve component 118 coupled to commissural posts 134. Valve component 118 typically comprises a pliant material. The pliant material is configured to collapse inwardly (i.e., towards the central longitudinal axis) during diastole, in order to inhibit retrograde blood flow, and to open outwardly during systole, to allow blood flow through the prosthesis.

Valve prosthesis 130 is configured to be implanted in a native diseased valve of a patient, such as a native stenotic aortic or pulmonary valve, using a minimallyinvasive approach, such as a beating heart endovascular retrograde transaortic, e.g. transfemoral, procedure. Support frame 140 is typically compressed so that its diameter is reduced in order to facilitate loading into a delivery tube, and, optionally, an introducer sheath, for delivery to the native valve site during a minimally-invasive delivery procedure, as described hereinbelow with reference to FIGS. 2A-B, 3A-C, 4A-B, 5A-C, and 6A-B. Support frame 140 is configured such that application of radial forces thereon radially compress the frame, reducing the frame's outer diameter. Upon removal of the radial forces, the frame assumes its previous uncompressed diameter and shape, i.e., the frame is self-expanding. The prosthesis is compressed by loading it into a delivery tube sufficiently small to allow transluminal delivery to the patient's native valve site. Support frame 140 comprises a suitable material that allows mechanical deformations associated with crimping and expansion of valve prosthesis 130, such as, but not limited to, a superelastic material, such as nitinol, or a stainless steel alloy (e.g., AISI 316).

Support frame 140 is typically shaped to define an upstream section 122, a throat section 124, and a downstream section 126. The cross-sectional area of upstream section 122 gradually decreases from an upstream end thereof to a downstream end adjacent to throat section 124. The cross-sectional area of throat section 24 is typically less than that of the aortic annulus of the intended patient. The cross-sectional area of downstream section 126 gradually increases to an area greater than that of throat section 124. Thus the cross-sectional areas of both the upstream and downstream sections are greater than that of the throat section. Throat section 124 is configured to be placed within the leaflet section of the native valve, slightly above the aortic annulus at the ventriculo-aortic border, such that downstream section 126 is located in the aorta, such as in the aortic sinuses. Typically, throat section 124 is configured to exert an outward radial force against the native leaflets, in order to prevent blood leakage between the valve prosthesis and the native valve. Such outward radial force typically does not substantially aid with fixation of the valve prosthesis at the native valve complex, and typically does not radially squeeze the native valve leaflets between the throat section any other elements of valve prosthesis 130.

Typically, support frame is elastic, and is shaped so as to define a plurality of collapsible cells. For example, the support frame may be fabricated by cutting a solid tube. The cells may be diamond-shaped, parallelogram-shaped, or otherwise shaped to be conducive to crimping the frame. Downstream section 126 is shaped so as to define upstream inlet 131, which is configured to apply an axial force directed toward the ascending aorta. Typically, when prosthesis 130 assumes an uncompressed implantation state, upstream inlet 131 has a greatest diameter of at least 20 mm, such as at least 26 mm, and of no more than 32 mm, such as no more than 30 mm. Optionally, inlet 131 is shaped so as to define one or more barbs positioned circumferentially such that the barbs pierce the native vale annulus in order to provide better anchoring (configuration not shown). Typically, valve prosthesis 130 further comprises inlet covering 135 which is coupled to upstream inlet 131, such as by sewing the covering within the inlet (configuration shown in FIG. 1A) or around the inlet (configuration not shown). Inlet covering 135 may comprise, for example, polyester or a processed biological material, such as pericardium. Support frame 140 thus defines a central structured body for flow passage that terminates in an upstream direction in a flared inlet (upstream inlet 131) that is configured to be seated within an LVOT immediately below an aortic annulus/aortic valve. Typically, the upstream axial force applied by downstream section 126 and the downstream axial force applied by upstream inlet 131 together anchor valve prosthesis 130 to the native valve complex.

In an embodiment of the present invention, support frame 140 is shaped so as to define a plurality of downstream axial support extensions 128, such as described in a U.S. provisional patent application to Tuval et al., filed Sep. 15, 2008, entitled, "Prosthetic heart valve for transfemoral delivery," which is assigned to the assignee of the present application and is incorporated herein by reference. The downstream axial support extensions join a downstream side of upstream inlet 131, and extend in a downstream direction at a first angle with respect to the central longitudinal axis of valve prosthesis 130, while commissural posts 134 extend in a downstream direction at a second angle with respect to axis 116. The first angle is greater than the second angle. Because of this greater angle, downstream axial support extensions 128: (a) apply an upstream axial force to a downstream side of the native leaflet tips, (b) do not touch the leaflets of the flexible prosthetic valve component when the prosthetic valve component is in its open position, and (c) provide stability to support frame 140. The first angle may, for example, be between about 15 and about 45 degrees, such as about 130 degrees, while the second angle may, for example, be between about 1 and about 15 degrees, such as about 8 degrees.

For some applications, support frame 140 is shaped so as to define a plurality of upper sinus support elements 136, which extend in a downstream direction. Upper sinus support elements 136 are configured to rest against the upper aortic sinuses (i.e., the downstream portion of the aortic sinuses) upon implantation of valve prosthesis 130, so as to provide support against tilting of the prosthesis with respect to the central longitudinal axis thereof. Typically, the downstream-most portions of upper sinus support elements 136 are bent toward the central longitudinal axis of the prosthesis to avoid damage to the walls of the upper sinuses. For some applications, support frame 140 is shaped so as to define exactly three downstream axial support extensions 128 and exactly six upper sinus support elements 136.

In an embodiment of the present invention, a portion of the cells of support frame 140 are shaped to define a plurality of outwardly-extending short axial support arms, which extend radially outward and upstream from the central longitudinal axis of valve prosthesis 130, such as described in U.S. Provisional Application 60/978,794, filed Oct. 10, 2007, entitled, "Prosthetic heart valve specially adapted for transfemoral delivery," and the above-mentioned U.S. provisional application to Tuval et al., both of which are assigned to the assignee of the present application and are incorporated herein by reference.

Although exactly three commissural posts 134 are shown in the figures, for some applications valve prosthesis 130 comprises fewer or more posts 134, such as two posts 134, or four or more posts 134. It is noted that approximately 90% of humans have exactly three aortic sinuses. The three posts provided in most embodiments correspond to these three aortic sinuses. For implantation in the approximately 10% of patients that have exactly two aortic sinuses, prosthesis 130 typically includes exactly two posts.

Figure 2A:
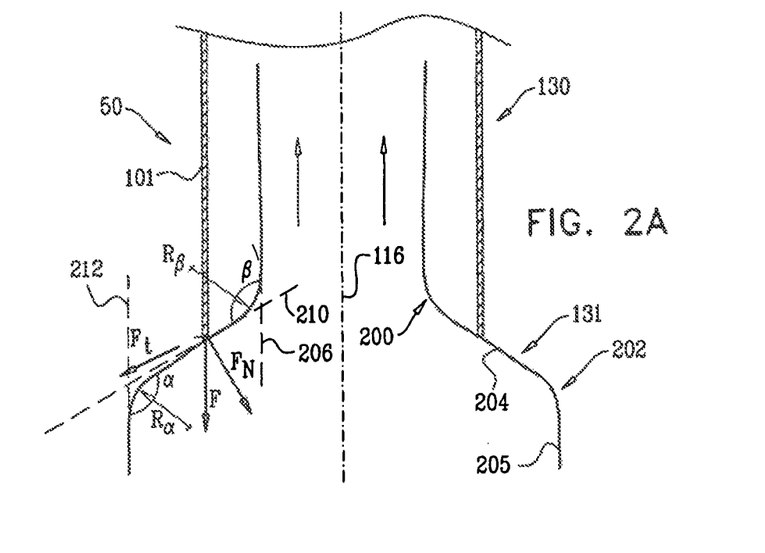
FIGS. 2A and 2B are schematic cross-sectional illustrations of the valve prosthesis of FIGS. 1A-C in an uncompressed implantation state and a partially-compressed delivery state, respectively, in accordance with an embodiment of the present invention.
Figure 2B:
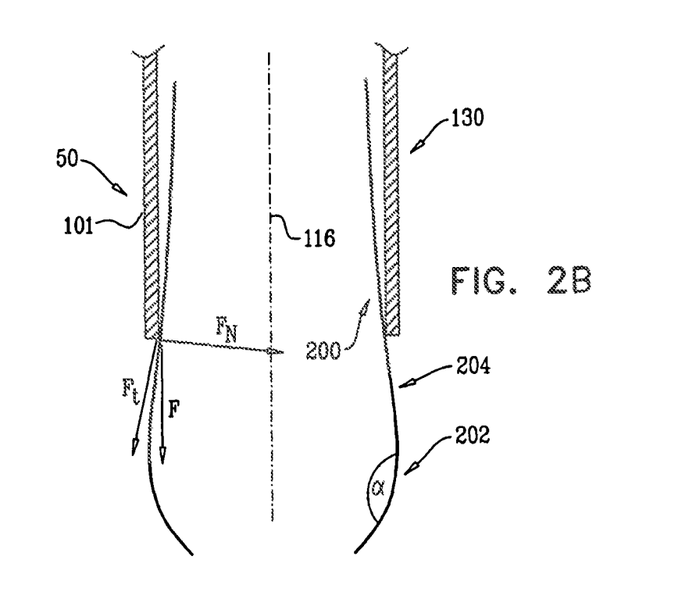

FIGS. 2A and 2B are schematic cross-sectional illustrations of valve prosthesis 130 in an uncompressed implantation state and a partially-compressed delivery state, respectively, in accordance with an embodiment of the present invention. In the uncompressed implantation state, upstream inlet 131 generally assumes the shape of a bell characterized a first downstream curved portion 200 and a second upstream curved portion 202, which are connected by an intermediary portion 204, which may be straight (as shown in FIGS. 2A and 2B) or slightly curved (configuration not shown). An upstream-most portion 205 of the inlet extends in an upstream direction from second upstream curved portion 202. A delivery system 50 for delivering valve prosthesis 130 to a target site and implanting the prosthesis at the site comprises a delivery tube 101.

As shown in FIG. 2A, first curved portion 200 curves outwardly from central longitudinal axis 116 of prosthesis 130 (which coincides with the central longitudinal axis of delivery tube 101), while second curved portion 202 curves inwardly toward the axis, typically such that upstream-most portion 205 is parallel to axis 116. At first curved portion 200, (a) a first line 206 parallel to central longitudinal axis 116 defines an angle β with respect to (b) a second line 210 that is tangential to both curved portions 200 and 202. Angle β is typically between about 90 and about 170 degrees, such as between about 100 and about 135 degrees. First curved portion 200 typically has a radius of curvature Rβ of between about 1 and about 15 mm, such as between about 4 and about 10 mm. At second curved portion 202, (a) a third line 212 generally parallel with upstream-most portion 205 defines an angle α with respect to (b) second line 210. Angle α is typically between about 90 and about 170 degrees, such as between about 100 and about 135 degrees. Second curved portion 202 typically has a radius of curvature Rα of between about 1 and about 15 mm, such as between about 4 and about 10 mm.

As prosthesis 130 is retracted into a delivery tube 101, the tube exerts a force F on intermediary portion 204 of the inlet. Force F has two force vector components: (1) Ft, which acts in a direction generally parallel to portion 204, and (2) Fn, which acts in a direction generally orthogonal to portion 204.

In the partially-compressed state shown in FIG. 2B, delivery tube 101 thus forces the inlet to bend around first curved portion 200, thus moving the portion of the inlet upstream to the point at which delivery tube 101 applies force F toward central longitudinal axis 116. The shape of the fully compressed upstream portion inlet (as shown, for example, in FIGS. 3A-C) depends in large part on the curvature of curved portion 202.

Figure 3A:
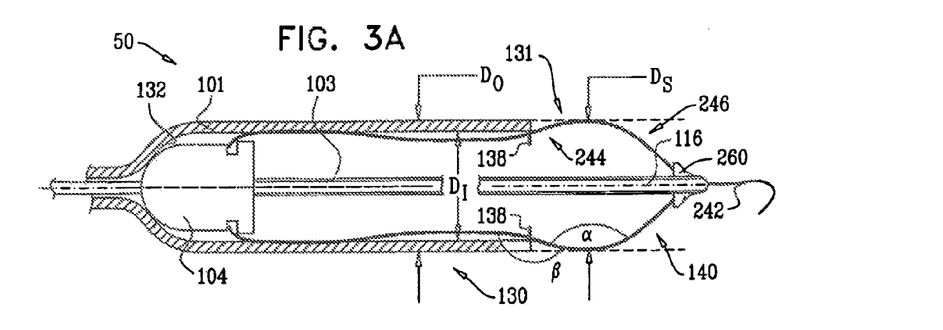
FIGS. 3A-C are schematic cross-sectional illustrations of the valve prosthesis of FIGS. 1A-C in a compressed delivery state partially within a delivery tube, in accordance with respective embodiments of the present invention.
Figure 3B:
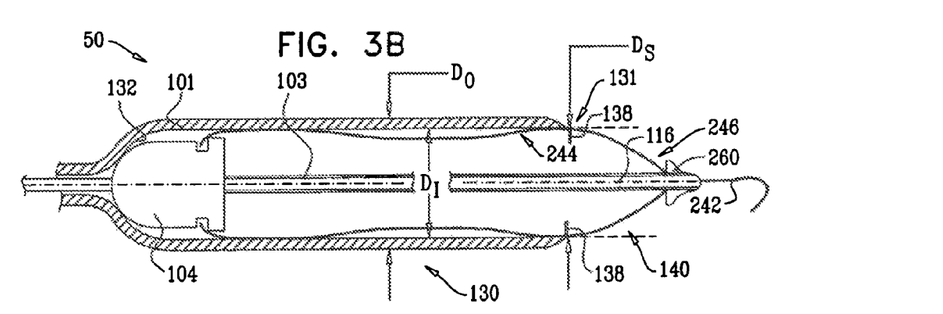
Figure 3C:
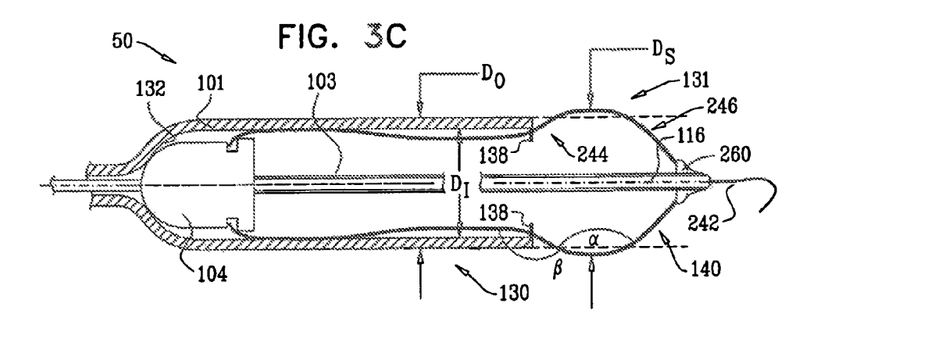

Reference is made to FIGS. 3A-C, which are schematic cross-sectional illustrations of valve prosthesis 130 in the compressed delivery state partially within delivery tube 101, in accordance with respective embodiments of the present invention. Delivery system 50 further comprises a valve holder 104 and a neutral tube 103 that is concentric with delivery tube 101. Valve prosthesis 130 is partially held between delivery tube 101 and neutral tube 103. Delivery system 50 is used to effect the release of valve prosthesis 130 by moving delivery tube 101 with respect to neutral tube 103.

Valve prosthesis 130 is configured to assume its compressed delivery state upon being placed partially within delivery tube 101, such that support frame 140 extends at least partially outside of the delivery tube in an upstream direction. Typically, at least a portion of upstream inlet 131 extends outside of the delivery tube. For example, the portion of the upstream inlet that extends outside of the delivery tube may have an axial length that is greater than 20% of an axial length of the support structure when the valve prosthesis assumes the compressed delivery state. Optionally, the entire upstream inlet extends outside of the delivery tube. Providing an appropriate angle a and an appropriate radius of curvature Ra ensures that the upstream-most portions of the compressed inlet converge towards central longitudinal axis 116, rather than being oriented generally parallel with the axis.

Typically, upstream-most portions 246 of the inlet converge to within 2 mm of the axis, such as within 1 mm of the axis. For some applications, one or more (e.g., all) of the upstream-most portions of the inlet converge at the axis. (The upstream-most portions typically comprise cells of frame 140.) For some applications, as shown in the figures, the upstream ends of inlet 131 rest against neutral tube 103. Typically, all parts of the inlet within 1 mm of the upstream end of the inlet are within 2 mm of the axis, such as within 1 mm of the axis. For some applications, upstream inlet 131 has a greatest outer diameter that is no greater than 6 mm, such as no greater than 4.5 mm, when the prosthesis assumes the compressed delivery state.

For some applications, delivery tube 101 is configured to aid in properly positioning valve prosthesis 130 partially within the delivery tube at a desired depth of insertion. The delivery tube may comprise or be shaped so as to define a stopper portion 132, typically at a downstream end of the tube, that blocks further insertion of the prosthesis into the delivery tube. For example, valve holder 104 may be configured to come in contact with stopper portion 132. Alternatively or additionally, valve prosthesis 130 has a marking 138 that indicates a desired depth of insertion in a downstream direction of the valve prosthesis into the delivery tube.

A diameter of a downstream portion 244 of inlet 131 outside of delivery tube 101 increases along an upstream direction (towards the right in FIGS. 3A-C), while a diameter of upstream-most portions 246 of the inlet monotonically decreases along the upstream direction, i.e., tapers inwardly toward central longitudinal axis 116.

For some applications, such as in the configuration shown in FIG. 3A, a greatest outer diameter DS of inlet 131 is greater than or equal to an outer diameter DO of delivery tube 101, when the prosthesis assumes the compressed delivery state. This wide portion of the inlet prevents direct exposure of the upstream end of delivery tube 101 (which may be sharp) to the vasculature, the native stenotic aortic valve, and an introducer sheath (as described hereinbelow), as the delivery tube and the prosthesis are advanced toward the implantation site. In addition, because outer diameter DO of delivery tube 101 is greater than an inner diameter DI thereof, this wide portion of the inlet need not be compressed as much as would be necessary if it were to be inserted into delivery tube 101. Furthermore, this bulging configuration (in which DS is greater than DO) enables the use of an introducer sheath (as described hereinbelow) having an internal diameter less than that of the bulging portion of the inlet, because the bulging portion of the compressed inlet (which is free of delivery tube 101) can be further radially compressed by insertion into the introducer sheath. When, during an implantation procedure, delivery tube 101 and valve prosthesis 130 exit the introducer sheath and enter the patient's blood vessel (typically the iliac artery), the vessel has a diameter greater than the diameter of the bulging portion of the crimped prosthesis, which allows this bulging portion to expand, without coming in contact with the wall of the vessel, which is larger at this point in this vasculature. An introducer sheath can be used that fits delivery tube 101, while allowing greatest outer diameter DS of inlet 131 to be greater than outer diameter DO of delivery tube 101.

For other applications, such as in the configuration shown in FIG. 3B, the portion of inlet 131 having the greatest diameter, when in its compressed delivery state, is within delivery tube 101, such that greatest outer inlet diameter DS is equal to inner diameter DI of delivery tube 101.

For still other applications, such as the configuration shown in FIG. 3C, greatest outer diameter DS of the downstream bulging portion is greater than outer diameter DO of delivery tube 101. An introducer sheath, as described hereinbelow, may still have an inner diameter equal to or only slightly larger than outer diameter DO of the delivery tube (e.g., less than 0.2 mm greater than DO, such as less 0.1 mm greater than DO), because insertion of the downstream bulging portion of the inlet into the introducer sheath compresses the bulging portion, completing the compression of the prosthesis, as described hereinbelow with reference to FIGS. 5A-C. Not compressing the inlet entirely within delivery tube 101 results in loading and unloading forces that are less would result if the inlet were inserted entirely into the delivery tube.

Reference is again made to FIGS. 3A-C. In an embodiment of the present invention, a small delivery tip 260 is removably coupled to neutral tube 103 such that the upstream-most portions of inlet 131 rest against a downstream side of the delivery tip when the prosthesis assumes the collapsed delivery state partially inserted in delivery tube 101. Delivery tip 260 is not coupled to delivery tube 101. The tip covers the upstream-most portions, which may be sharp. The delivery tip typically has a length of less than 10 mm, e.g., less than 5 mm, and a maximum diameter of less than 4 mm, e.g., less than 3 mm. The tip is shaped so as to define a longitudinal opening therethrough, through which a guidewire 242 slides during the delivery procedure. Typically, inlet tip 131 prevents the upstream-most ends of inlet 131 from scraping against the blood vessel or the introducer sheath. Although these upstream-most ends may rest against neutral tube 103, they may still scrape because of their thickness.

Figure 4A:
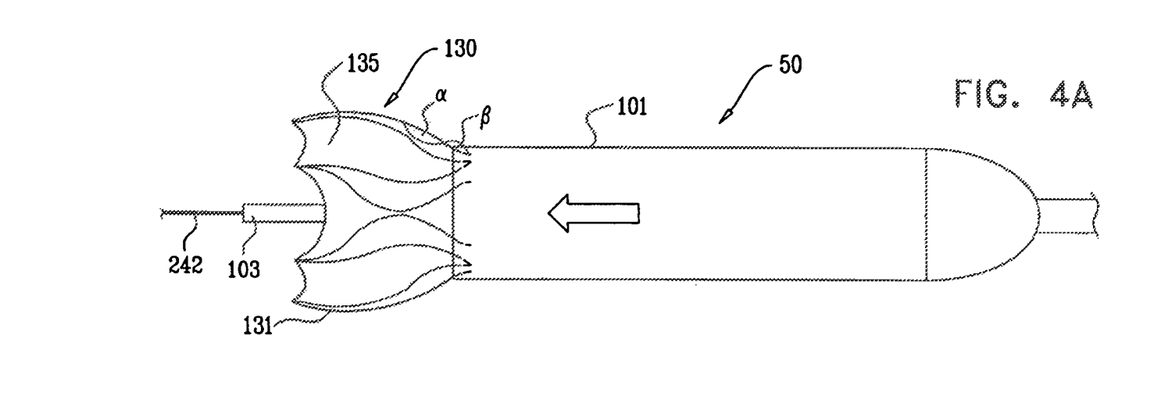
FIGS. 4A and 4B are schematic illustrations showing the valve prosthesis of FIGS. 1A-C in partially-compressed and compressed states, respectively, in accordance with an embodiment of the present invention.
Figure 4B:
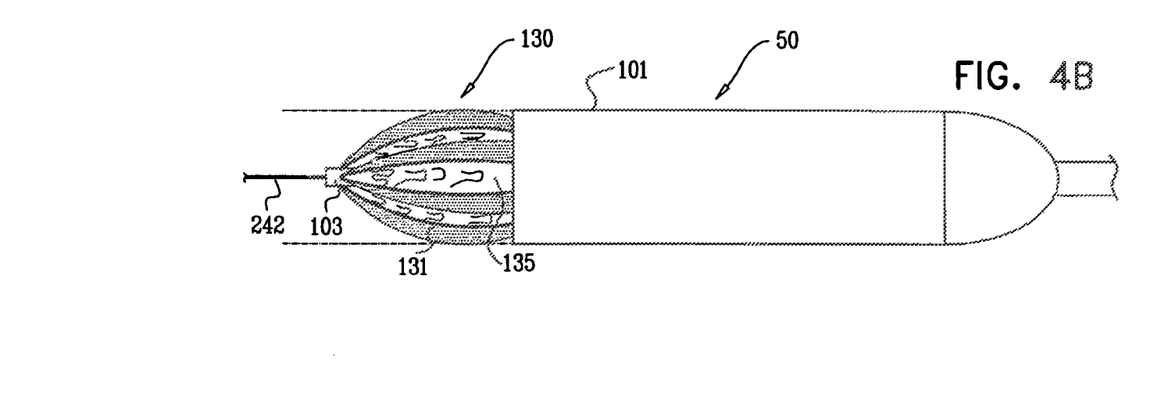

Reference is made to FIGS. 4A and 4B, which are schematic illustrations showing valve prosthesis 130 in partially-compressed and compressed states, respectively, in accordance with an embodiment of the present invention. In the compressed state shown in FIG. 4B, the greatest outer diameter of inlet 131 is equal to the outer diameter of delivery tube 101.

Figure 5A:
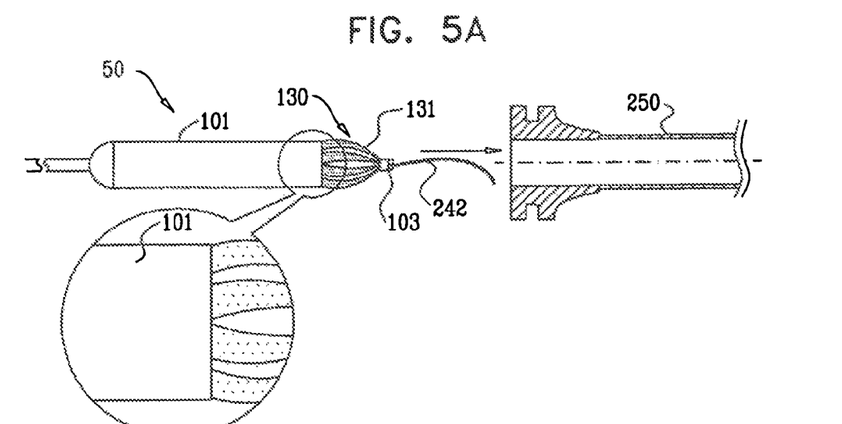
FIGS. 5A-C are schematic illustrations of the valve prosthesis of FIGS. 1A-C and a delivery tube in several stages of insertion into an introducer sheath, in accordance with an embodiment of the present invention.
Figure 5B:
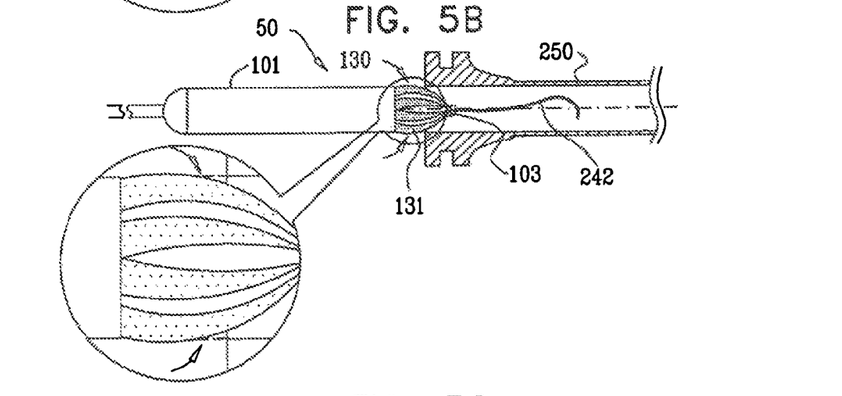
Figure 5C:
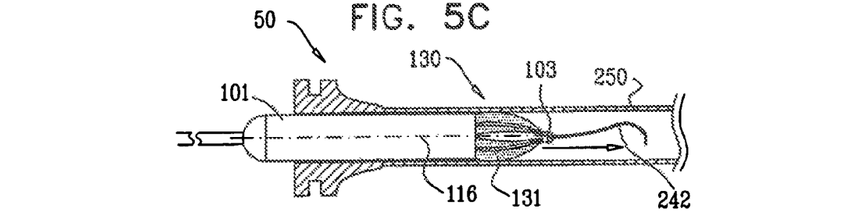

Reference is made to FIGS. 5A-C, which are schematic illustrations of valve prosthesis 130 and delivery tube 101 in several stages of insertion into an introducer sheath 250, in accordance with an embodiment of the present invention. In this embodiment, introducer sheath 250, such as a femoral introducer sheath, is provided for aiding delivery of valve prosthesis 130. The introducer sheath is used to advance delivery tube 101 and valve prosthesis 130 into the vasculature, and at least partially through the vasculature toward the ascending aorta. Typically, during an implantation procedure, the introducer sheath is inserted into the femoral artery, and advanced until a distal end of the sheath reaches the iliac artery, the descending aorta, or the ascending aorta. The valve prosthesis, which is loaded into the delivery tube, is then inserted into the sheath and advanced therethrough until it exits the distal end of the sheath in the iliac artery, descending aorta, or ascending aorta. The prosthesis and delivery tube are then further advanced until they reach the site of the native valve complex.

As in the configuration described hereinabove with reference to FIG. 3C, in the configuration shown in FIGS. 5A-C the greatest outer diameter of the downstream bulging portion of inlet 131 is greater than the outer diameter of delivery tube 101, when the prosthesis assumes the compressed delivery state and prior to its insertion into sheath 250, as shown in FIG. 5A FIG. 5B shows inlet 131 partially inserted into the sheath, such that the inlet is partially compressed by the sheath. FIG. 5C shows inlet 131 fully inserted into the sheath, such that the greatest outer diameter of the inlet has been reduced to the inner diameter of the sheath, which is approximately equal to the outer diameter of delivery tube 101. Inlet 131 thus has a greatest outer diameter that is greater than the outer diameter of delivery tube 101 before the inlet is inserted into the sheath, and approximately the same as the outer diameter of delivery tube 101 after the inlet has been inserted into the sheath. After the prosthesis and delivery tube pass through the sheath and exit the distal end of the sheath, inlet 131 once again assumes an outer diameter greater than that of the delivery tube. (Upon release from delivery tube 101, inlet 131 assumes an even greater diameter for implantation at the native valve complex.)

Figure 6A:
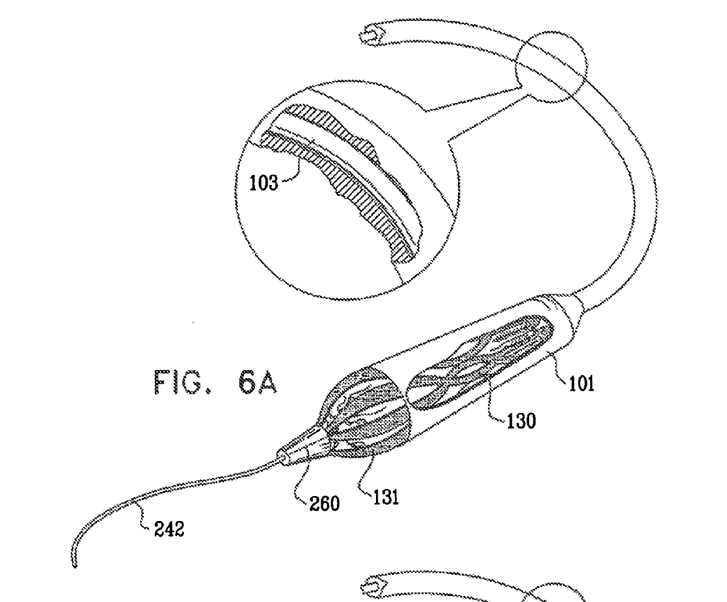
FIGS. 6A and 6B are perspective schematic illustrations of the prosthesis of FIGS. 1A-C in its compressed state, in accordance with respective embodiments of the present invention.
Figure 6B:
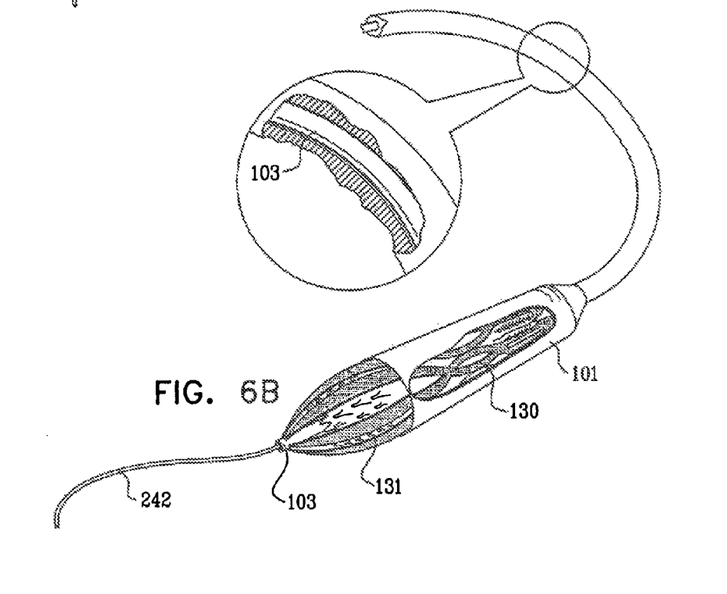

FIGS. 6A and 6B are perspective schematic illustrations of prosthesis 130 in its compressed state, in accordance with respective embodiments of the present invention. In the embodiment shown in FIG. 6A, delivery tip 260 is provided, as described hereinabove with reference to FIG. 3A-C. As can be seen, the delivery tip is not coupled to delivery tube 101. In the embodiment shown in FIG. 6B, the delivery tip is not provided. The upstream-most portions of inlet 131 converge toward a central longitudinal axis of the prosthesis, and rest against neutral tube 103 of delivery system 50.

In an embodiment of the present invention, during an implantation procedure delivery tube 101 is inserted into a body lumen, such as a femoral artery, and guided over guidewire 242 through the ascending aorta and over an aortic arch, until the tip of the guidewire passes into a left ventricle. Optionally, the stenotic aortic valve is partially dilated to about 15-20 mm (e.g., about 16 mm), typically using a standard valvuloplasty balloon catheter. The upstream-most portion of valve prosthesis 130 is advanced past the native aortic valve leaflets into the left ventricle. At this stage of the procedure, delivery tube 101 is located between the native aortic leaflets.

Delivery tube 101 is withdrawn a predetermined distance to expose upstream inlet 131 of valve prosthesis 130. Delivery tube 101 moves with respect to inner tube 103, such that valve prosthesis 130 and inner tube 103 are partially exposed from the catheter. Inlet 131 is positioned within the left ventricle.

Delivery tube 101 is withdrawn until inlet 131 abuts firmly against the ventricular side of the aortic annulus and/ or the aortic valve leaflets. Delivery tube 101 is further withdrawn until the tube is located just upstream of the ends of commissural posts 134 of valve prosthesis 130, such that the commissural posts are still held firmly by delivery tube 101. Valve prosthesis 130 is completely released from delivery tube 101. Support frame 140, which is typically superelastic, rapidly expands to its fully opened position, pushing the native valve leaflets radially outward. Prosthetic valve 130 is thus released with the delivery tube being moved in only one direction during the entire procedure, which facilitates the implantation procedure significantly.

For some applications, prosthesis 130 is implanted using some of the techniques described with reference to FIGS. 9A-G in U.S. application Ser. No. 12/050,628, filed Mar. 18, 2008, entitled, "Valve suturing and implantation procedures," which is incorporated herein by reference, and/or using some of the techniques described in the above-mentioned US provisional application to Tuval et al.

Figure 7:
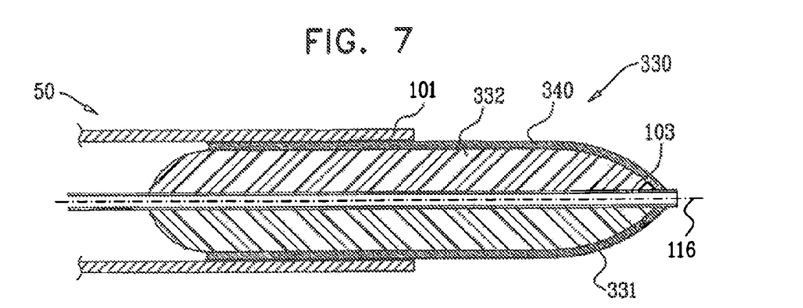
FIG. 7 is a schematic illustration of a balloon-inflatable valve prosthesis, in accordance with an embodiment of the present invention.

FIG. 7 is a schematic illustration of a balloon-inflatable valve prosthesis 330, in accordance with an embodiment of the present invention. In this embodiment, delivery system 50 comprises a shaped balloon 332 for plastically deforming a support structure 340 of valve prosthesis 330, to give the structure a non-cylindrical shape. In this embodiment, support structure 140 may comprise a stainless steel alloy which is plastically deformed during compression, thereby reducing the valve diameter, and mounted onto the balloon prior to implantation. When the delivery catheter is in place in the patient, shaped balloon 332 is used to open the compressed prosthesis into place, and to give it a non-cylindrical shape. The prosthesis is configured to be compressed partially within a delivery tube for transluminal delivery. An upstream inlet 331 of the prosthesis is shaped such that when the prosthesis is compressed partially within delivery tube 101, an upstream portion of the inlet is tapered in an upstream direction toward central longitudinal axis 116 of the prosthesis. Upstream-most portions of the inlet converge to within 2 mm of the axis, e.g., within 1 mm of the axis, e.g., at the axis. Typically, all parts of the inlet within 1 mm of the upstream end of the inlet are within 2 mm of the axis, e.g., within 1 mm of the axis.

In the present patent application, including in the claims, the word "downstream" means near or toward the direction in which the blood flow is moving, and "upstream" means the opposite direction. For embodiments in which the valve prosthesis is implanted at the aortic valve, the aorta is downstream and the ventricle is upstream. As used in the present patent application, including in the claims, the "native valve complex" includes the native semilunar valve leaflets, the annulus of the valve, the subvalvular tissue on the ventricular side, and the lower half of the semilunar sinuses. As used in the present application, including in the claims, a "native semilunar valve" is to be understood as including: (a) native semilunar valves that include their native leaflets, and (b) native semilunar valves, the native leaflets of which have been surgically excised or are otherwise absent.

Although prosthesis 130 is generally described herein as being implanted in an aortic position, the techniques described herein, as appropriately modified, may also be used to implant the prosthesis in other locations, such as in a pulmonary valve.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. patent application Ser. No. 11/024,908, filed Dec. 30, 2004, entitled, "Fluid flow prosthetic device," which issued as U.S. Pat. No. 7,201,772;

International Patent Application PCT/IL2005/001399, filed Dec. 29, 2005, entitled, "Fluid flow prosthetic device," which published as PCT Publication WO 06/070372;

International Patent Application PCT/IL2004/000601, filed Jul. 6, 2004, entitled, "Implantable prosthetic devices particularly for transarterial delivery in the treatment of aortic stenosis, and methods of implanting such devices," which published as PCT Publication WO 05/002466, and U.S. patent application Ser. No. 10/563, 384, filed Apr. 20, 2006, in the national stage thereof, which published as US Patent Application Publication 2006/0259134;

U.S. Provisional Application 60/845,728, filed Sep. 19, 2006, entitled, "Fixation member for valve";

U.S. Provisional Application 60/852,435, filed Oct. 16, 2006, entitled, "Transapical delivery system with ventriculo-arterial overflow bypass";

U.S. patent application Ser. No. 11/728,253, filed Mar. 23, 2007, entitled, "Valve prosthesis fixation techniques using sandwiching";

International Patent Application PCT/IL2007/001237, filed Oct. 16, 2007, entitled, "Transapical delivery system with ventriculo-arterial overflow bypass," which published as PCT Publication WO 2008/047354;

U.S. patent application Ser. No. 12/050,628, filed Mar. 18, 2008, entitled, "Valve suturing and implantation procedures";

a U.S. provisional application filed Sep. 15, 2008, entitled, "Prosthetic heart valve having identifiers for aiding in radiographic positioning";

U.S. Provisional Application 60/978,794, filed Oct. 10, 2007, entitled, "Prosthetic heart valve specially adapted for transfemoral delivery";

a U.S. provisional application filed Sep. 15, 2008, entitled, "Prosthetic heart valve for transfemoral delivery";

U.S. patent application Ser. No. 12/248,776, filed Oct. 9, 2008, entitled, "Prosthetic heart valve for transfemoral delivery."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

It is understood that the examples and embodiments described herein are for illustrative purposes only and that various modifications or changes in light thereof will be suggested to persons skilled in the art and are to be included within the spirit and purview of this application and scope of any appended claims. All figures, tables, and appendices, as well as publications, patents, and patent applications, cited herein are hereby incorporated by reference in their entirety for all purposes.

What is claimed is:

1. Apparatus comprising a valve prosthesis for attachment to a native valve complex of a subject, the prosthesis configured to assume a compressed delivery state and an uncompressed implantation state, the prosthesis comprising:

a support frame, which is shaped so as to define an upstream inlet having upstream-most ends that are tapered in an upstream direction toward a central longitudinal axis of the prosthesis when the prosthesis assumes the compressed delivery state, wherein the upstream-most ends of the inlet converge to within 2 mm of the central longitudinal axis when the prosthesis assumes the compressed delivery state; and a flexible prosthetic heart valve component, coupled to the support frame.

2. The apparatus according to claim 1, wherein the upstream inlet has a greatest outer inlet diameter of at least 20 mm when the prosthesis assumes the uncompressed implantation state.

3. The apparatus according to claim 1, wherein the support frame is shaped so as to define a downstream section that is configured to apply an upstream axial force to a downstream side of the native valve complex, wherein the upstream inlet is configured to apply a downstream axial force on an upstream side of the native valve complex, and wherein the valve prosthesis is configured such that the upstream and downstream axial forces together anchor the valve prosthesis to the native valve complex.

4. The apparatus according to claim 1, wherein the upstream-most ends of the inlet converge at the central longitudinal axis when the prosthesis assumes the compressed delivery state.

5. The apparatus according to claim 1, wherein at least one of the upstream-most ends of the inlet converges at the central longitudinal axis when the prosthesis assumes the compressed delivery state.

6. The apparatus according to claim 1, wherein all parts of the inlet within 1 mm of an upstream end of the inlet are within 2 mm of the central longitudinal axis when the prosthesis assumes the compressed delivery state.

7. The apparatus according to claim 1, further comprising a delivery tube, wherein the prosthesis is configured to assume the compressed delivery state upon placement of the valve prosthesis partially within the delivery tube.

8. The apparatus according to claim 7, wherein the delivery tube is configured to prevent full insertion of the valve prosthesis into the delivery tube.

9. The apparatus according to claim 7, wherein the valve prosthesis has a marking that indicates a desired depth of insertion in a downstream direction of the valve prosthesis into the delivery tube.

10. The apparatus according to claim 7, wherein when the prosthesis assumes the uncompressed implantation state, the support frame is shaped so as to define two curved portions connected by an intermediary portion, such that when the intermediary portion is subjected to an upstream axial force applied by the delivery tube when the prosthesis is placed partially within the delivery tube, resulting vector component forces compress the upstream inlet toward the central longitudinal axis.

11. The apparatus according to claim 2, further comprising a delivery tube, wherein the prosthesis is configured to assume the compressed delivery state upon placement of the valve prosthesis partially within the delivery tube.

12. The apparatus according to claim 3, further comprising a delivery tube, wherein the prosthesis is configured to assume the compressed delivery state upon placement of the valve prosthesis partially within the delivery tube.

13. Apparatus comprising a valve prosthesis for attachment to a native valve complex of a subject, the prosthesis configured to assume a compressed delivery state and an uncompressed implantation state, the prosthesis comprising:
- a support frame, which is shaped so as to define an upstream inlet having upstream-most ends that are tapered in an upstream direction toward a central longitudinal axis of the prosthesis when the prosthesis assumes the compressed delivery state;
- a flexible prosthetic heart valve component, coupled to the support frame; and
- a delivery tube, wherein the prosthesis is configured to assume the compressed delivery state upon placement of the valve prosthesis partially within the delivery tube, and wherein when the prosthesis assumes the compressed delivery state, a portion of the upstream inlet that extends outside of the delivery tube has a greatest outer inlet diameter that is greater than an outer tube diameter of the delivery tube.

14. Apparatus comprising a valve prosthesis for attachment to a native valve complex of a subject, the prosthesis configured to assume a compressed delivery state and an uncompressed implantation state, the prosthesis comprising:
- a support frame, which is shaped so as to define an upstream inlet having upstream-most ends that are tapered in an upstream direction toward a central longitudinal axis of the prosthesis when the prosthesis assumes the compressed delivery state;
- a flexible prosthetic heart valve component, coupled to the support frame; and
- a delivery tube, wherein the prosthesis is configured to assume the compressed delivery state upon placement of the valve prosthesis partially within the delivery tube, and wherein when the prosthesis assumes the compressed delivery state, a portion of the upstream inlet that extends outside of the delivery tube has a greatest outer inlet diameter that is equal to an outer tube diameter of the delivery tube.

15. The apparatus according to claim 13, wherein the upstream-most ends of the inlet converge to within 2 mm of the central longitudinal axis when the prosthesis assumes the compressed delivery state.

16. The apparatus according to claim 14, wherein the upstream-most ends of the inlet converge to within 2 mm of the central longitudinal axis when the prosthesis assumes the compressed delivery state.

17. The apparatus according to claim 15, wherein all parts of the inlet within 1 mm of an upstream end of the inlet are within 2 mm of the central longitudinal axis when the prosthesis assumes the compressed delivery state.

18. The apparatus according to claim 16, wherein all parts of the inlet within 1 mm of an upstream end of the inlet are within 2 mm of the central longitudinal axis when the prosthesis assumes the compressed delivery state.

* * * * *